US008346371B2

(12) United States Patent
Weiss et al.

(10) Patent No.: US 8,346,371 B2
(45) Date of Patent: Jan. 1, 2013

(54) ELECTRODE UNIT FOR CARRYING CURRENT OR VOLTAGE BETWEEN AN IMPLANTABLE ELECTROMEDICAL DEVICE AND A TREATMENT AND/OR DIAGNOSIS SITE IN THE HUMAN BODY

(75) Inventors: Ingo Weiss, Berlin (DE); Michael Friedrich, Kleinmachnow (DE); Stefan Knorr, Berlin (DE); René Fischer, Berlin (DE); Marc Steffen Schurr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 149 days.

(21) Appl. No.: 13/017,915

(22) Filed: Jan. 31, 2011

(65) Prior Publication Data

US 2011/0196461 A1 Aug. 11, 2011

(30) Foreign Application Priority Data

Feb. 11, 2010 (DE) ........................ 10 2010 000 373

(51) Int. Cl.
*A61N 1/00* (2006.01)

(52) U.S. Cl. ........................................................ 607/115

(58) Field of Classification Search .................. 607/115, 607/116, 119; 600/423, 424; 333/175; 361/54; 324/318
See application file for complete search history.

(56) References Cited

U.S. PATENT DOCUMENTS

| | | | | |
|---|---|---|---|---|
| 7,363,090 | B2 | 4/2008 | Halperin | |
| 2008/0058902 | A1 | 3/2008 | Gray et al. | |
| 2008/0058913 | A1 | 3/2008 | Gray et al. | |
| 2008/0147154 | A1* | 6/2008 | Gray et al. | 607/115 |
| 2010/0114277 | A1* | 5/2010 | Zhao et al. | 607/116 |
| 2012/0161901 | A1* | 6/2012 | Stevenson et al. | 333/175 |

FOREIGN PATENT DOCUMENTS

EP 2025361 A1 2/2009

OTHER PUBLICATIONS

European Search Report dated May 6, 2011 (6 pages).

* cited by examiner

*Primary Examiner* — George Manuel
*Assistant Examiner* — Robert N Wieland
(74) *Attorney, Agent, or Firm* — ARC IP Law, PC; Joseph J. Mayo

(57) ABSTRACT

An electrode unit for carrying current or voltage between an implantable electromedical device and a treatment and/or diagnosis site in the human body comprises at least one current-/voltage-carrying feed line (1) and at least one electric contact pole to the body part. The feed line (1) is associated with at least one section (4) having frequency-dependent transmission behavior, wherein this at least one frequency-dependent transmission section (4) at least partially filters out therapeutically and/or diagnostically undesirable signals in at least one defined frequency range.

8 Claims, 16 Drawing Sheets

ELECTRODE UNIT FOR CARRYING CURRENT OR VOLTAGE BETWEEN AN IMPLANTABLE ELECTROMEDICAL DEVICE AND A TREATMENT AND/OR DIAGNOSIS SITE IN THE HUMAN BODY

This application takes priority from German Patent Application DE 10 2010 000 373.5, filed 11 Feb. 2010, the specification of which is hereby incorporated herein by reference.

BACKGROUND OF THE INVENTION

1. Field of the Invention

The technical field is related to an electrode unit for carrying current or voltage between an implantable electromedical device and a treatment and/or diagnosis site in the human body, wherein the electrode unit comprises at least one current-/voltage-carrying feed line and at least one electric contact pole to the body part.

2. Description of the Related Art

With respect to the background of the invention, it is noted that the subject matter of embodiments of the invention is primarily relevant in connection with cardiac pacemakers, implantable defibrillators, and other types of active implantable electromedical devices. The latter generally comprise at least one current-/voltage-carrying feed line in the electrode unit—typically referred to in short as the "electrode—, the distal end of which is disposed in a ventricle, for example, and used to measure cardiological potential signals or deliver appropriate therapeutic current signals.

The compatibility of such electrode units in implantable electromedical devices with radio frequency magnetic fields, as they are used in particular in imaging diagnostic methods based on magnetic resonance—referred to as MRI (magnetic resonance imaging) methods—represents a serious problem. Using such MRI methods, a strong static magnetic field is superimposed with an alternating magnetic field pulsed with radio frequency (RF), which is used to change the energy status of the protons in the examined tissue and produce appropriate MRI signals from the tissue.

According to the laws of electromagnetic induction, this alternating magnetic field results in alternating voltages in the feed line of the electrode units of electromedical device implants in question here, the energy of these alternating voltages being converted into heat, notably at the electrically conductive contact poles of the electrode unit with the human tissue. This may lead to considerable heating, for example of the tip contact of a cardiac electrode, along with corresponding impairment and even damage of the heart tissue in contact therewith or surrounding the same.

In order to prevent this problem, it is proposed in U.S. Pat. No. 7,363,090 B2 to use filters based on resonant circuits comprising an inductor connected in parallel with a capacitor, which is associated with the corresponding feed line for the tip contact pole or a ring contact pole of a particular electrode of an implantable electromedical device. In the practical implementation of the patent holder, the filters disclosed in this known patent are designed as comparatively bulky components that stiffen the electrode unit over a certain length and therefore lead to unfavorable mechanical properties in the electrode equipped therewith. Furthermore the filter is accommodated in a closed housing, which does not provide any leadthrough for the guide wires generally used when implanting an electrode. In this respect, the application possibilities of this known electrode comprising a filter device are limited.

BRIEF SUMMARY OF THE INVENTION

A feature of one or more embodiments of the invention is to improve electrode units of this type, as those which are implemented by cardiac pacemaker electrodes, for example, in such a way that filter measures can be implemented without considerably impairing the practical application possibilities.

This is achieved in the most general form by the characterizing features as claimed herein. According to this, the current-/voltage-carrying feed line of the electrode unit is associated with at least one section having frequency-dependent transmission behavior, wherein this at least one frequency-dependent transmission section at least partially filters out therapeutically and/or diagnostically undesirable signals in at least one defined frequency range.

Because of this frequency-dependent transmission behavior, the electrode unit is adjusted to filter out alternating voltages harmful in a magnetic resonance environment due to the alternating magnetic field and to effectively suppress heating of the feed line to the electric contact pole of the electrode unit. In this respect, no undesirable currents flow in the body of the patient. Filtering out frequencies or frequency ranges, as provided according to the invention, may also be manifested in a redistribution of the induced alternating currents in the feed line between different contact poles, which likewise effectively prevents heating of the feed line and contact poles.

According to preferred refinements of the invention, the frequency-dependent transmission behavior may correspond to a low-pass, band-stop, band-pass, or high-pass filter. The low-pass characteristic may have a cut-off frequency of 100 kHz, for example, with 10 kHz being particularly preferred, having an slope of >=6 db/octave. In the case of a band-stop filter, the frequency stop band may range between 10 MHz and 3 Ghz. This frequency characteristic is equally advantageous for the frequency-dependent transmission behavior of implanted electromedical devices to the treatment/diagnosis site as the above-mentioned low-pass behavior.

For the frequency-dependent transmission behavior between different contact poles at the treatment/diagnosis site, the above-mentioned high-pass characteristic having a cutoff frequency of >100 kHz and a slope of >6 db/octave or low-pass behavior with a center frequency between 10 MHz and 3 Ghz is advantageous. The filter grade of a band-stop or high-pass filter should be higher than 20.

With respect to the conductor forming the current-/voltage-carrying element, it should be noted that this conductor comprises insulation having direct current conductivity that is at least 100 times lower than the conductor itself. The latter may generally be made of metal or conductive plastic, carbon fibers, conductive fluid and the like.

According to a preferred embodiment of the invention, the frequency-dependent transmission system may comprise a leadthrough having preferably a minimum diameter of 0.2 mm for a guide wire, mandrin or the like. Contrary to the prior art, the electrode unit according to the invention can thus be introduced into relevant body vessels by way of a guide wire, despite the filtration of the induced voltages.

In general, the frequency-dependent transmission system may contact one or more feed lines in the implantable electrode unit. The transmission system is then connected to the feed line at suitable positions of the same.

According to a particularly suitable refinement, the frequency-dependent transmission system is formed directly by one or more sections of the current-/voltage-carrying feed line, which can be implemented, for example, by a section of a helix of the feed line that has higher conductivity. Preferably the electrical conductivity of an appropriate section of the helical feed line should be at least twice as high as the surrounding regions of the feed line. The higher conductive design of the corresponding helical section may be caused by a highly conductive coating or doping of the helix material in this section. The windings in the higher conductive section of the helix should preferably be insulated to the outside, whereby short circuits between the individual windings of the helix are prevented.

An advantageous design of an appropriate frequency-dependent transmission system is implemented by an inductance-capacitance (LC) resonator, wherein the higher conductive section of the helix is combined as the inductance with a capacitor connected in parallel. The higher conductive helical section implementing the inductance is preferably gold-plated, for example, so as to ensure high quality of the LC resonant circuit.

A very compact refinement of such an LC resonator is obtained by one variant of the invention, wherein the capacitor is formed by a cylinder capacitor disposed around the conductive section of the helix and/or inside the conductive section of the helix. This constitutes a particularly compact embodiment of the electrode unit according to the invention, wherein the helix interior remains available as a leadthrough for a guide wire and/or the same is used for the configuration.

According to a further preferred refinement of the invention, the frequency dependence of the transmission system can be variably controlled. To this end, the electrode unit can be adjusted to the respective circumstances, this being the frequency of the induced interference signals. The electrode unit thus remains universally usable, regardless of the MRI environment.

The frequency dependence is preferably controlled by way of a trim element, such as a voltage-controlled capacitor, a so-called varicap or a varactor. Bias voltage may also be employed to control the frequency. Such a control voltage can be generated directly by programming the electromedical device or by a sensor for detecting therapeutically and/or diagnostically undesirable signals. The sensor may detect interference frequency in a predetermined frequency band and/or with a specific amplitude that is larger than a settable threshold. In this respect, an electrode unit of an implantable electromedical device may be used in a plurality of conventional magnetic field ranges of MRI systems, these being 1.5 and 3.0 T, for example, unlike a hard-wired variant.

Different preferred variants exist for the positioning of the sensor, for example it may be disposed directly in the implanted electromedical device or it may be associated with the feed line of the electrode unit. In the first case, appropriate control lines lead to the frequency-dependent transmission system to control the frequency dependence thereof.

When associating the sensor with the feed line, the sensor operates substantially self-sufficiently, this being without the implantable electromedical device, thereby reducing the wiring complexity to control the frequency dependence. Advantageously a field sensor for electrical, magnetic and/or electromagnetic fields is used as the sensor, wherein the fields are static and/or alternating fields, notably in the form of a dipole.

A further variant for the frequency-dependent transmission system is by forming the same by an resonant circuit. The frequency-dependent transmission behavior is then implemented, as needed, by electrically active elements in the form of a resistor R, a capacitor C, inductor L or using transmitters Ü. To this end, active element combinations such as RL, RC, RLC, RÜ, CÜ or RLCÜ are employed. One or more of such resonant circuits can be combined, wherein preferably inductive coupling to one or more feed lines is possible.

A connection of the frequency-dependent transmission system having a suitable design is possible by designing the system on a fixing helix at the electrode unit. An inductor is in particular formed by part of the fixing helix.

A further design variant for the frequency-dependent transmission system is to implement it with one or more waveguides having frequency-specific wave impedance. The waveguide concept may be used alone or in combination with other frequency control mechanisms, such as the above-mentioned resonant circuits.

The waveguide is, or the waveguides are, preferably terminated by a terminating impedance, which in the simplest case is a short circuit.

So as to adjust the frequency to at least two undesirable signal frequencies, networks may be interposed in the waveguide or waveguides and/or a waveguide may be terminated by a network. In this way, high variability in the frequency adjustment can be achieved.

In principle, any waveguide can be formed by two conductors that are coupled by a dielectric.

A compact design for associating the waveguide with a current-/voltage-conducting feed line is provided by a helical configuration of the waveguide and integration in a current-/voltage-conducting feed line configured as a helical line.

In addition to the embodiments described herein other alternative embodiments may include some or all of the disclosed features.

BRIEF DESCRIPTION OF THE DRAWINGS

Further characteristics, details and advantages of the invention will be apparent from the descriptions of a plurality of embodiments provided hereinafter based on the enclosed drawings. In the drawings.

DETAILED DESCRIPTION OF THE INVENTION

Figure 1:
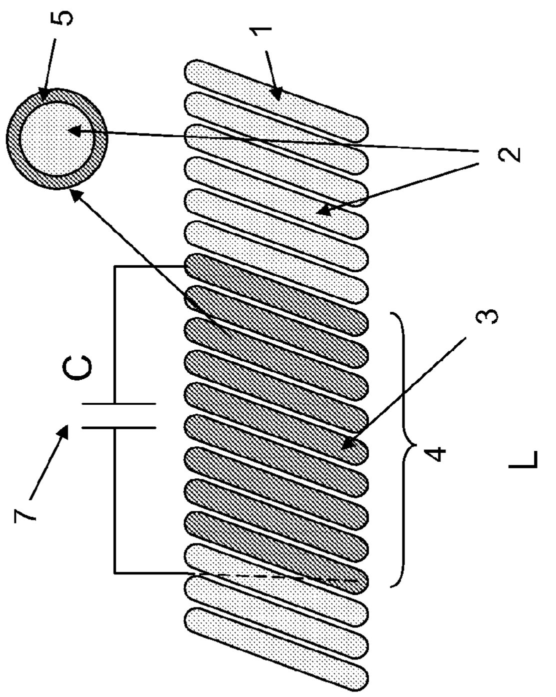
FIG. 1 shows a schematic view of a feed line of an electrode unit for carrying current or voltage between an implantable electromedical device and a treatment and/or diagnosis site, comprising an integrated frequency-dependent transmission system, and a detailed cross-section of the feed line.

In connection with an electrode unit, which is not shown as a whole, for carrying current or voltage between an implantable electromedical device and a treatment and/or diagnosis site, as it is represented by a cardiac pacemaker electrode, for example, FIG. 1 shows substantially only a feed line 1, which is configured in the form of a helix 2 made of conventional surgical steel, such as MP35N. The feed line 1 leads to an electrical contact pole, which is not shown and which is in electrical contact with a body part and represented, for example, by a tip or ring contact pole of the cardiac pacemaker electrode.

The basic concept of the present invention is apparent from FIG. 1 in that a system 3 having frequency-dependent transmission behavior is provided, which at least partially filters out therapeutically and/or diagnostically undesirable signals in at least one defined frequency range, for example over 10 MHz, and thereby avoids the problems described above when a radio-frequency alternating magnetic field acts on the electrode unit.

In the shown embodiment according to FIG. 1, the frequency-dependent transmission system 3 is formed by an LC resonant circuit, wherein the inductor L is formed by a section 4 extending over several windings of the helix 2 and made of considerably better, at least twice as electrically conductive material as the remaining helices. The higher conductivity is caused by a highly conductive coating 5, for example in the form of a gold plating—as is apparent from the detailed cross-section incorporated in FIG. 1. In this way, high quality of the resonant circuit 6 formed by the inductor L and the capacitor C connected in parallel thereto is ensured.

FIG. 2 shows the equivalent circuit of the frequency-dependent transmission system 3 in the form of an LC resonant circuit 6.

Figure 2A:
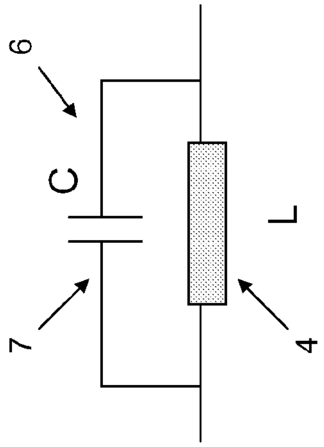
Figure 3:
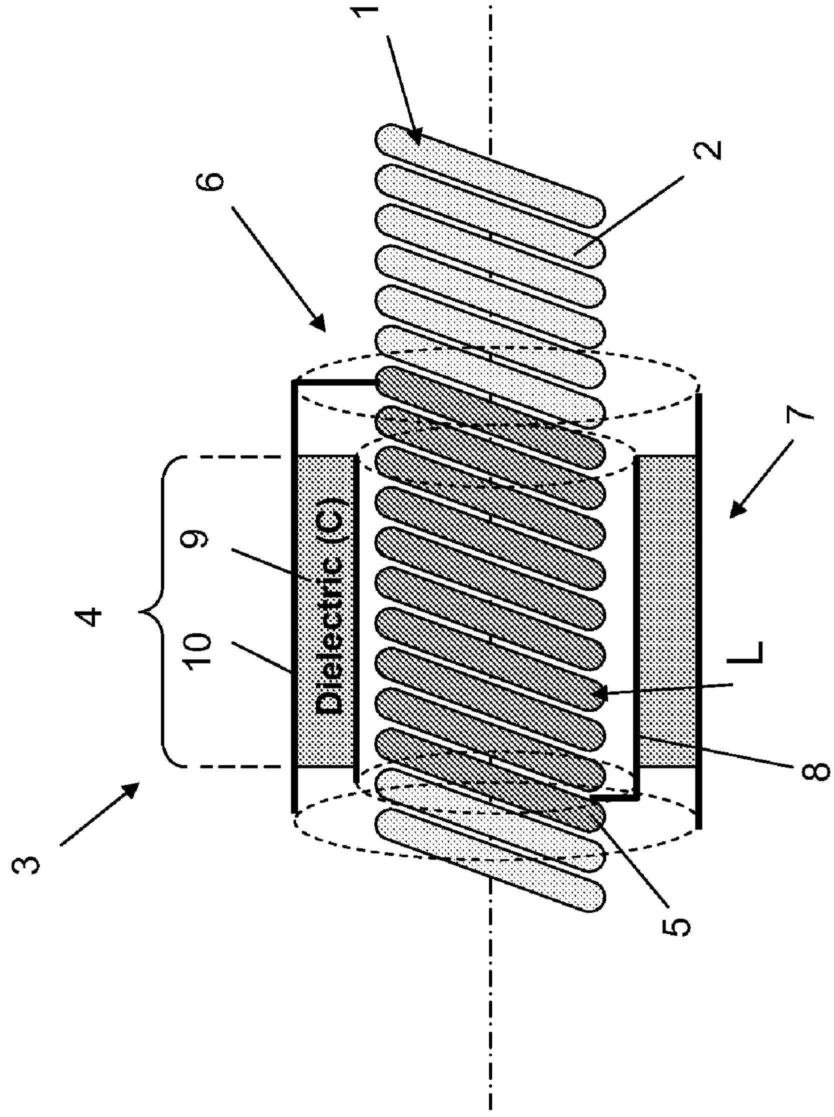
FIG. 3 shows a schematic illustration of a feed line having an integrated frequency-dependent transmission system in a further embodiment.

FIG. 3 shows schematically an implementation of the resonant circuit 6 comprising the described inductor L and a capacitor 7 disposed around the corresponding section 4 of the helix 2. The capacitor is implemented as a cylinder capacitor having an inner sleeve 8 and an outer sleeve 10 separated by a dielectric 9. Each of two sleeves 8, 10 is electrically connected to the helical windings at the opposing ends of the section 4, whereby the parallel circuit shown in FIG. 2*a* of the inductor L and capacitor C is created. The dielectric 9 has a dielectric value of eps_r>=2.5. Below eps_r=2.5, components become too large. The range of eps_r=2.5 to 10 covers the most common plastics, and even glass. Preferred is eps_r>=10 to 100 so as to keep the size small. This range also includes $Al_2O_3$ or $Ta_2O_5$, for example. A special embodiment relates to a sleeve having the oxide applied thereon by epitaxial growth, which also forms the dielectric ($Al_2O_3$ or $Ta_2O_5$ or oxides of other valve metals).

Also preferred would then be ceramics as the dielectric having eps_r>100 up to several thousand, for example barium titanate.

Figure 2B:
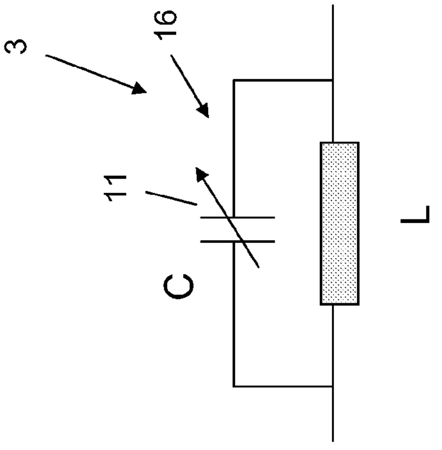
FIGS. 2A and 2B show equivalent circuits for the frequency-dependent transmission system in the form of an LC circuit having fixed and variable capacitances of the capacitor.

As is indicated in FIG. 2*b*, the frequency dependence of the frequency-dependent transmission system 3 may also be variably controllable, for example by the capacitor C being variable. The trimming of the capacitive element can be performed by the implant (not shown), this being a cardiac pacemaker or defibrillator, for example, using a bias voltage. The corresponding trim element 11 may be a voltage-controlled capacitor, varicap or varactor. The control parameters can be input into the implant by external programming.

Figure 4:
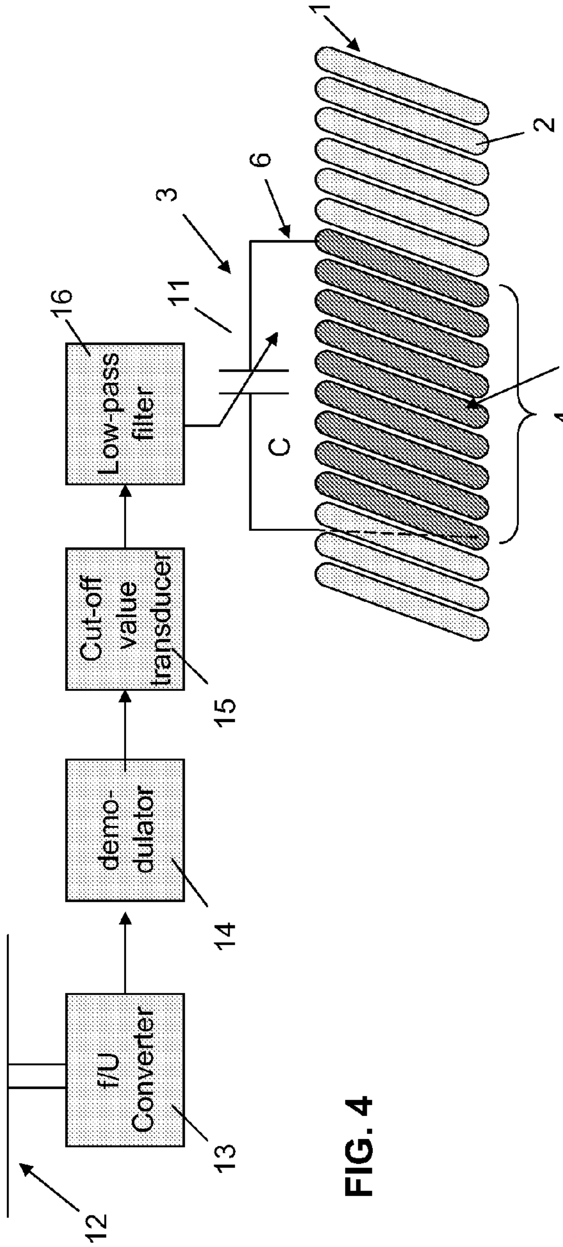
FIG. 4 shows a block diagram of a feed line comprising a transmission system having controllable frequency dependence.
Figure 5:
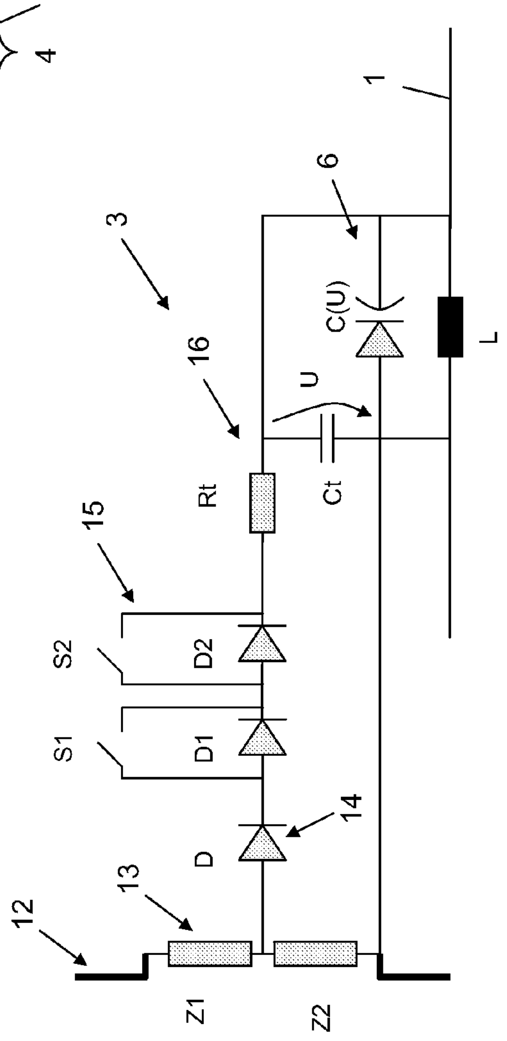
FIG. 5 is a circuit diagram of a circuit-related implementation of the assembly according to FIG. 4.

As an alternative, a sensor 12, notably a field sensor for the static magnetic field acting on the electrode unit, this being the intensity of the magnetic field and/or the frequency of an RF field, may be provided, which detects therapeutically and/or diagnostically undesirable signals. A corresponding electrode unit is shown in FIGS. 4 and 5. Downstream of the sensor 12 in the form of a dipole, a f/V converter (frequency-voltage converter) 13, a demodulator 14, a cut-off value transducer 15, and a low-pass filter 16 are connected. The trim element 11 can be set using the latter. Overall, the wiring of the trim element 11 shown in FIG. 4 detects interference frequency within a predetermined band and having an amplitude greater than a settable threshold. The corresponding parameters are geared to the customary magnetic fields, as they are used in known MRI systems having magnetic field strengths of 1.5 T and 3 T. The sensor 12 may be disposed in the implant, wherein control wires lead to the frequency-dependent transmission system 3, however the self-sufficient design shown in FIGS. 4 and 5 is to be preferred, wherein the sensor 12 is directly mounted in the region of the electrode unit.

FIG. 5 shows a specific implementation of the circuitry shown in a diagram-like manner in FIG. 4. The sensor 12 is a dipole, wherein the frequency/voltage (f/V) converter 13 is implemented by a voltage divider having two impedances Z1 and Z2. As an alternative, matched resonators can control the appropriate bias voltage for certain frequencies. In the example shown, Z1 would then be a resistor and Z2 an inductor.

The demodulator 14 is represented by a diode D, which is followed by a cut-off value transducer 15 in the form of the diodes D1, D2, which can be bypassed by switches S1, S2. The low-pass filter 16 is implemented as an RC circuit comprising the resistor Rt and the capacitor Ct.

The direct current smoothed in this way and corresponding to the applied magnetic field then controls the voltage-dependent capacitance C(V) of the resonant circuit 6. The inductance L thereof is in the electrode feed line 1.

The voltage-dependent capacitance C(V) may be implemented as a capacitance diode (tuning diode, varicap, varactor) or as described in EP 1 299 948 B1. Because the direct current V increases with the frequency f when designing the impedance Z1 as a resistor and the impedance Z2 as an inductor, the capacitance C(V) must be implemented such that the capacitance C decreases as the control voltage V rises, so that the effective frequency of the cut-off unit is increased. In the opposite case, the impedance Z2 would have to be selected as a resistor and the impedance Z1 as an inductor.

For the variant of a band-stop filter, it should be noted that the characteristic curve of the voltage-dependent capacitance C(V) is implemented so that the effective frequency of the frequency f detected with the field sensor 12 occurs. As an alternative, the frequency/voltage converter 13 may be designed with an accordingly compensative characteristic curve.

The possibility of adjusting the capacitance in such a way applies to all capacitances described in this application.

The variants of the invention described above can be outlined again briefly as follows:

- The sensor 12 is part of a control unit, which adjusts the frequency-dependent transmission behavior to the frequency of the currently present interference signal.
- The transmission system 3 having frequency-dependent transmission behavior can be implemented with active electrical elements, such as an RL, RC, RLC, RÜ, CÜ, RLCÜ circuit, with Ü denoting "transmitter".
- As will be explained hereafter, it is also possible to employ waveguides for the frequency-dependent transmission, which can optionally also be used in combination with the resonant circuitry described above.
- The active electrical elements are implemented by distributed parameters (material properties, e.g. a material that mechanically is one piece, but the material properties of which are locally distributed so that functionally specific electrical components are formed; e.g. sandwich composed of: conductive material, non-conductive material (notably having dielectric characteristics), conductive material form a capacitor in the flow direction of this enumeration)
- All measures described above may be combined.
- Attenuation, which can be implemented by one frequency-dependent transmission system, or as an overall effect of a plurality of frequency-dependent transmission systems, for the interference signals, may be more than 10 dB.
- The frequency-dependent transmission behavior (low-pass, high-pass, band-pass, band-stop) is implemented using resonant circuits or waveguides.
- The inductive elements (L, Ü) of the frequency-dependent transmission systems are implemented by utilizing existing inductive sections of the feed line 1, for example helices of pacemaker electrodes. Simple cable lines may also be coiled locally for this purpose.
- So as to increase the quality of the resonant circuit, and thereby increase the attenuation of the frequency-dependent transmission systems, conductors having high conductivity are used, for example copper, gold or silver wires. When using existing inductive sections of the feed line, the ohmic resistance thereof and therefore the power dissipation are reduced by applying highly conductive coatings to this section. This can be done by galvanizing or vapor deposition.
- The mechanical connection of the active electrical elements can be achieved using conventional measures, such as fixed connections in the form of welding, brazing or crimping. Mobile electrical connections can be achieved by way of sliding contacts, bendable intermediate elements or liquid-metal joints.

Figure 6:
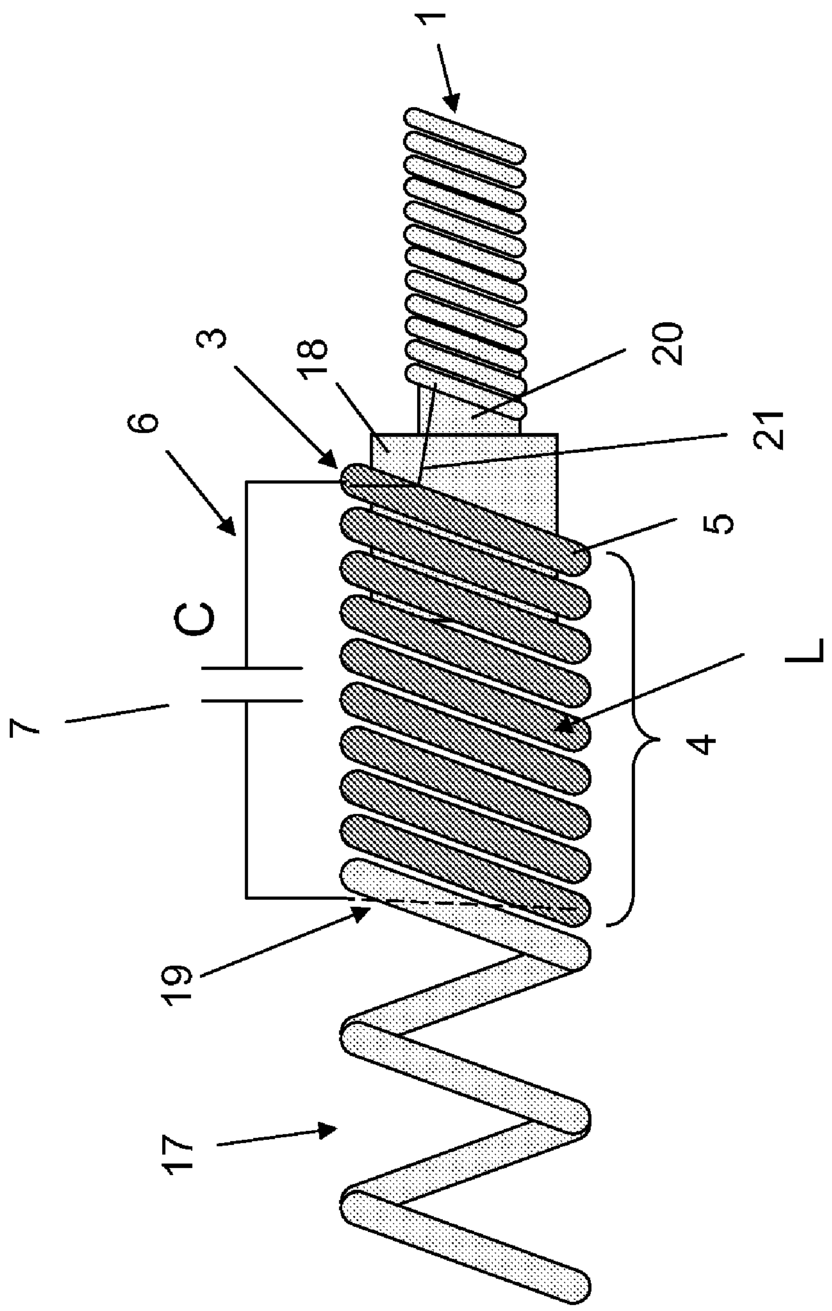
FIG. 6 shows a schematic view of a frequency-dependent transmission system integrated in a fixing helix of an electrode unit.

In the embodiment of an electrode unit shown in FIG. 6, the frequency-dependent transmission system 3 is integrated into what is referred to as a fixing helix 17, which represents the distal end of an electrode unit designed, for example, as a pacemaker electrode. As is apparent from the drawing, the feed line 1 transitions into a housing projection 18, to which the windings of the fixing helix 17 on the proximal side are fastened. Analogous to FIG. 1, the section 4 connecting to the fastening is again designed as an inductor L having an easily conductive coating 5 of the helical windings. The schematically indicated capacitor 7 having the capacitance C may be accommodated in the inside lumen 19 of the section 4 of the fixing helix 17, for example in the housing projection 18. The housing therefore thus forms the shoulder 20 to which the feed line 1 is fastened. An electrical connection 21 is provided between this shoulder and the section 4. The distal end of the fixing helix 17 is provided with axially widened windings, which can be "screwed" into the body tissue by rotating the fixing helix about the longitudinal axis thereof. The section 4 of the fixing helix 17 forming the inductor L is insulated toward the outside in the regions where it may have contact with the tissue. The contacting of the feed line 1 and the electrical connection 21 in the region of the shoulder are carried out by crimping.

Figure 7:
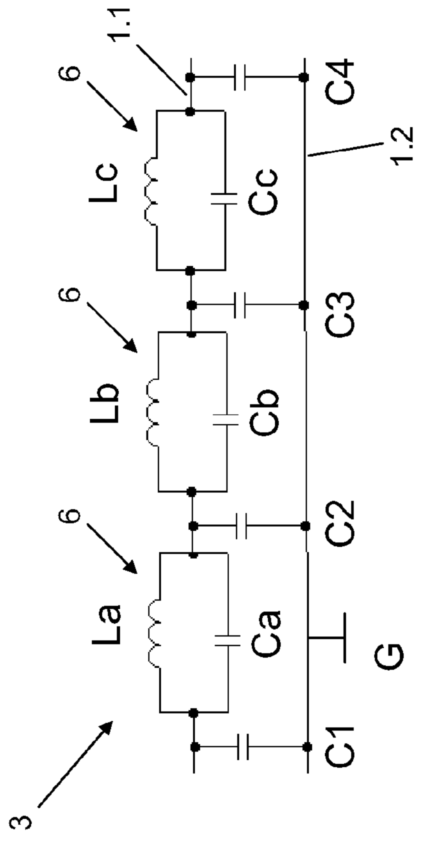
FIG. 7 shows a circuit diagram of an electrode unit having two feed lines and resonant circuits as frequency-dependent transmission systems.

FIG. 7 shows a first circuit-related implementation of the frequency-dependent transmission system 3 for two feed lines 1.1, 1.2, which employs resistors, inductors, capacitors, and transmitters. A higher-order elliptical low-pass filter is implemented, wherein series-connected parallel circuits of inductors La, Lb, Lc and capacitors Ca, Cb, Cc are cut in the feed line 1.1. The coupling to the feed line 1.2 is carried out by capacitors C1, C2, C3, C4 terminally and between the LC circuits. The feed line 1.1 supplies a contact pole of the electrode unit, while the second feed line 1.2 leads to a further contact pole, for example a ring electrode poles or an ICD shock coil. If no further such pole is present, the feed line 1.2 may also lead to a potential reference pole, which solely for this purpose is implemented as a contact to the tissue, but otherwise has no further function for diagnosis or treatment. In FIG. 7, the potential reference pole is denoted by G (ground).

Figure 8:
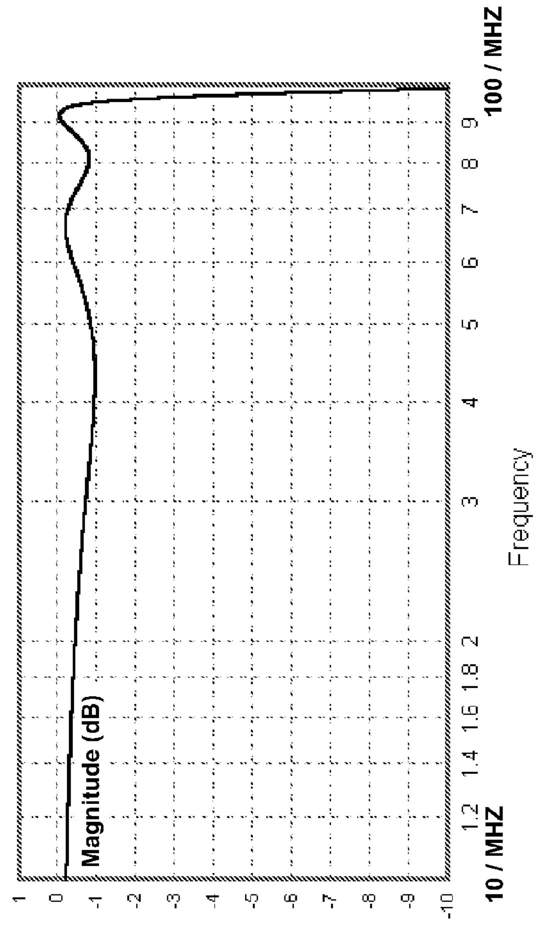
FIG. 8 shows the attenuation behavior of a frequency-dependent transmission system in the form of an $8^{th}$ order elliptical low-pass filter.

FIG. 8 shows by way of example the frequency response of a frequency-dependent transmission system between 10 and 100 MHz. It is apparent that, up to just before the cutoff frequency of 100 MHz, no relevant attenuation occurs, which then rises with a sharp slope to attenuation of >10 dB.

Figure 9:
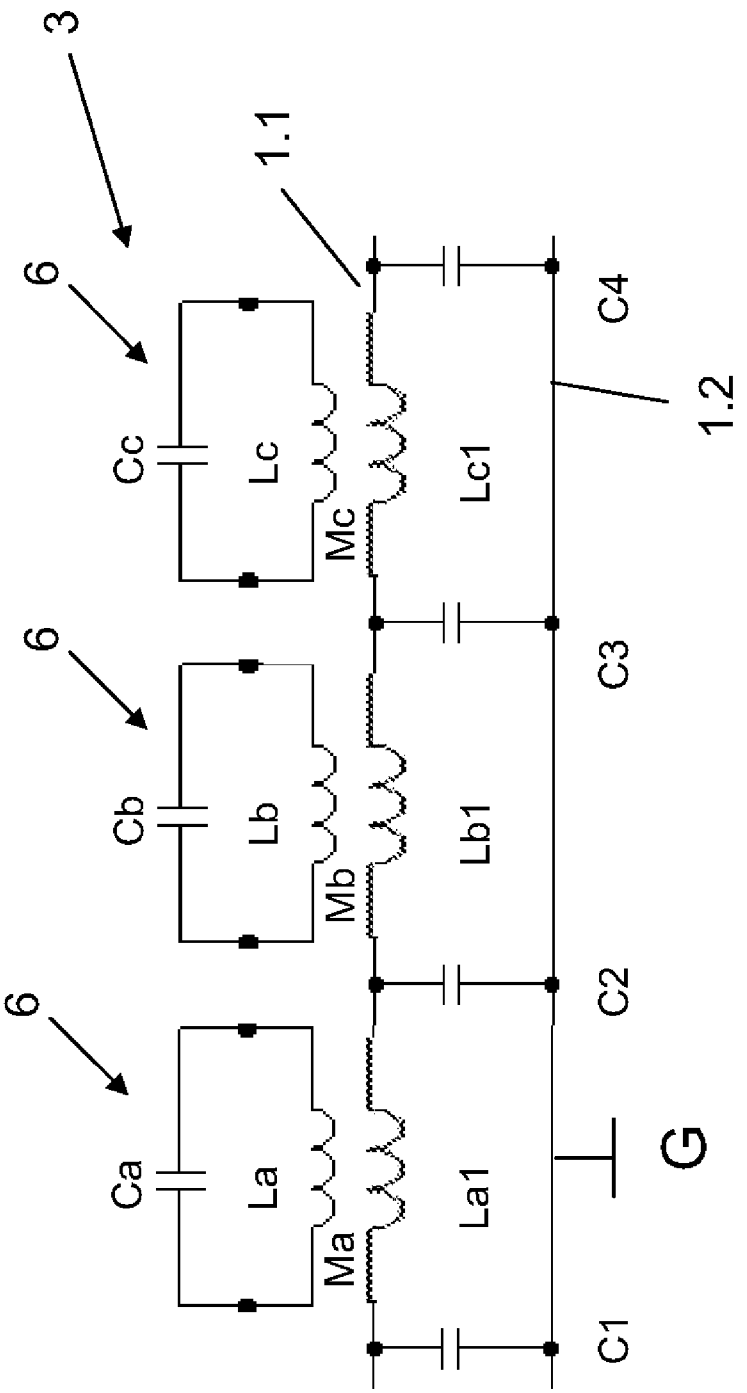
FIG. 9 shows a circuit diagram of an electrode unit having two feed lines and inductively coupled resonant circuits as the frequency-dependent transmission system.

FIG. 9 shows a frequency-dependent transmission system 3 having resonant circuits 6 in the form of LC resonators, which are inductively coupled into the feed line 1.1 by way of the inductors La, Lb, Lc via coupling inductors La1, Lb1, Lc1. Otherwise, the embodiment according to FIG. 9 corresponds to that of FIG. 7, so that reference is made to the description provided there.

Figure 10:
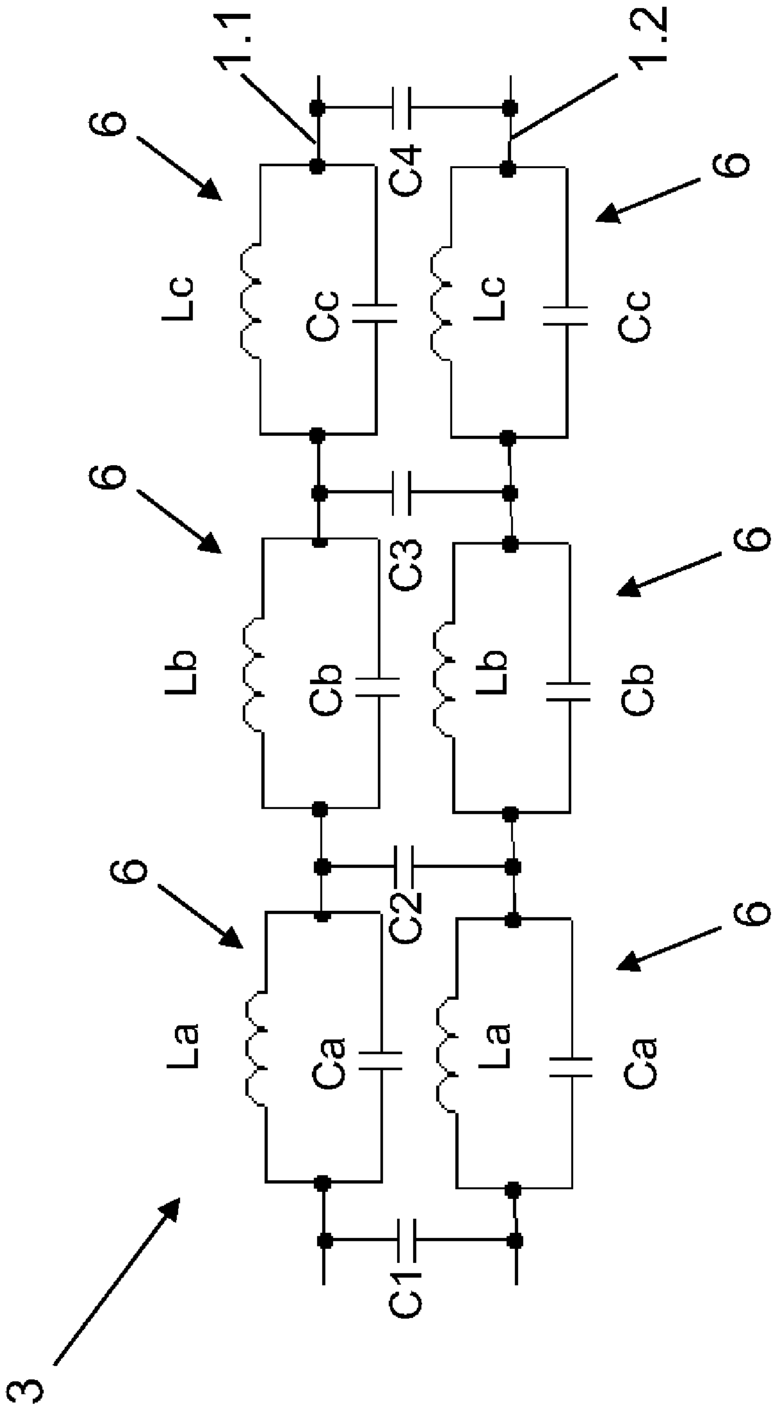
FIG. 10 is a variant of the electrode unit of FIG. 7 comprising resonant circuits integrated in both feed lines.

FIG. 10 shows a frequency-dependent transmission system 3, which is implemented in two feed lines 1.1, 1.2 to contact poles not shown in detail. In each feed line 1.1, 1.2, three resonant circuits 6, each having inductors La, Lb, Lc and capacitors Ca, Cb, Cc connected in parallel thereto, are connected in series. The two feed lines 1.1, 1.2 are furthermore capacitively coupled terminally and between the resonant circuits by capacitors C1, C2, C3, C4. In this design, symmetrically balanced low-pass filter properties are achieved.

Figure 11:
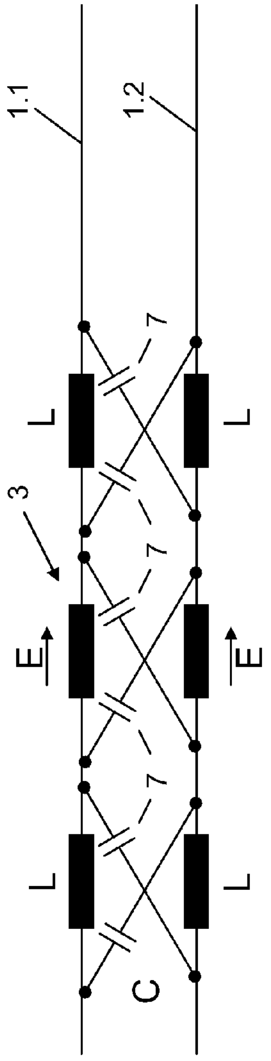
FIG. 11 shows a circuit diagram of an electrode unit having two feed lines, which comprise inductive sections and capacitive cross couplings.

FIG. 11 shows a frequency-dependent transmission system 3 for two feed lines 1.1, 1.2, wherein inductors L are cut in series in the feed lines 1.1, 1.2. The feed lines 1.1, 1.2 are then crosswise capacitively coupled by the capacitors 7 with the capacitance C, with respect to the respective inductances L.

The purpose of this type of wiring is that it largely eliminates voltages caused in the inductors by an alternating electromagnetic field. This is due to the fact that the two feed lines 1.1, 1.2 experience a substantially identical, tangential electrical field strength, because are located geometrically closely next to each other. The voltages caused in the inductors L are superimposed out of phase due to the crossed coupling by the capacitors 7, thereby causing a cancellation.

Figure 12:
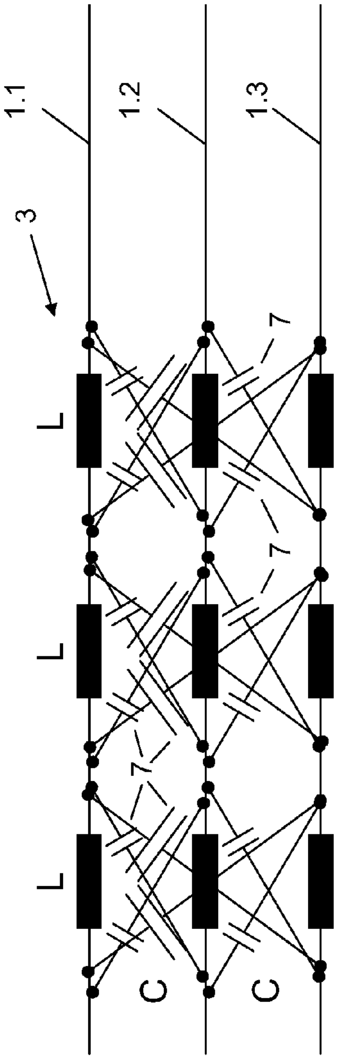
FIGS. 12 and 13 are analog circuit diagrams of electrode units having three feed lines.
Figure 13:
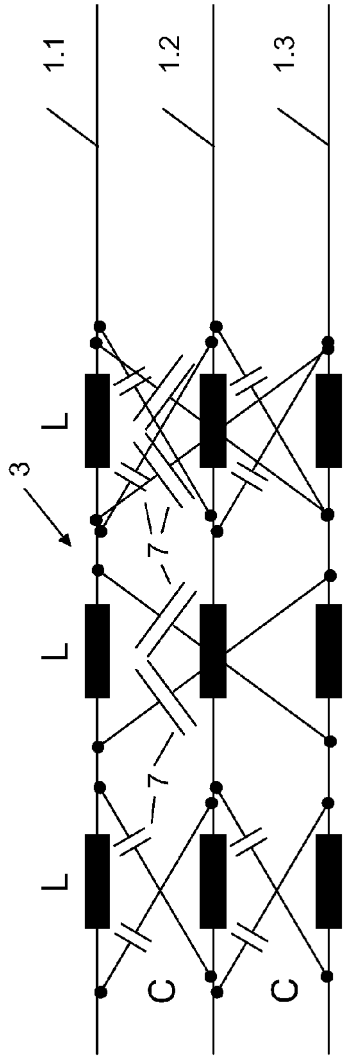
Figure 14:
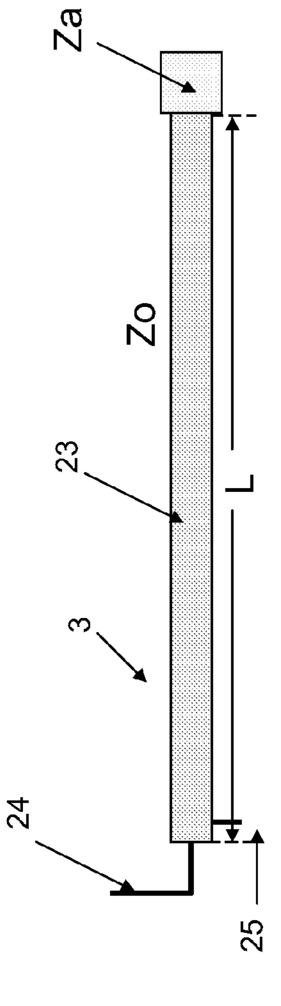
FIG. 14 is a schematic view of an electrode unit having two feed lines and a waveguide as the frequency-dependent transmission system.

An analogous cross-coupling of inductors in three feed lines 1.1, 1.2, 1.3 is shown in FIGS. 12 and 13. While in FIG. 12 all cross-combinations are coupled by capacitors 7, in the embodiment according to FIG. 13 some coupling capacitors have been omitted, which does not cause any significant impairment of the voltage cancellation.

FIGS. 14 to 22 show frequency-dependent transmission systems 3, which are based on the principle of waveguides. As is apparent from FIGS. 15 to 17, these waveguides 23 comprise two adjoining conductors 24, 25, which are coupled by a dielectric 26. The waveguide 23 is thereby characterized by specific wave impedance Z0. Depending on the terminating impedance Za connecting the two conductors 24, 25 of the waveguide 23, impedance Z develops at the opposing end between these conductors 24, 25. The terminating impedance Za can be implemented, for example, by a circuit of resistors R, inductors L, capacitors C, and transmitters Ü. The components should be dimensioned so that the desired impedance Z develops at the other when for a particular length l of the waveguide 23. In order to implement the filtration of a specific frequency, this being a cut-off, for example, Za and l must be designed so that, in the ideal case, Z simulates a disconnected line. In this case, a frequency-dependent power interruption exists. In the simplest, preferred case, Za is a short circuit, the low-frequency treatment and diagnosis currents can then flow without impairment. To this end, the length is determined as a function of the specific wave impedance Z0, for which purpose a "Smith chart" used.

In order to achieve good conductivity between two contact poles at a particular frequency, for example so as to redistribute undesirable parasitic currents, the procedure is exactly opposite to the explanations provided above. The terminator Za remains open, and over the length l of the waveguide 23 the impedance is then transformed so that, at the particular frequency, a frequency-dependent short circuit develops at the other end. This short circuit does not exist for low-frequency currents, so that the treatment and diagnosis are not influenced.

Figure 15:
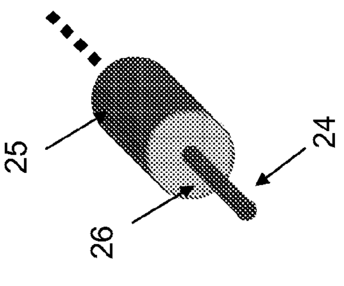
FIGS. 15-17 are schematic sectional perspective views of a waveguide in different implementations.

According to FIG. 15, the waveguide has a cylindrical design, wherein a coaxial inner conductor 24 and a tubular outer conductor 25 are coupled by the dielectric 26.

Figure 16:
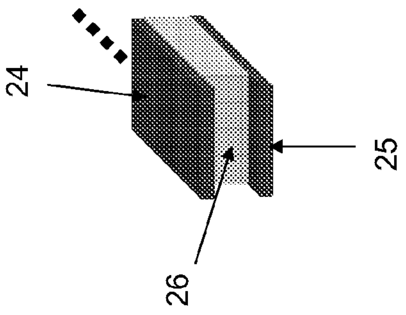

In the embodiment according to FIG. 16, planar, elongated conductors 24, 25 are disposed in a sandwich-like manner, having the dielectric 26 located in between.

Figure 17:
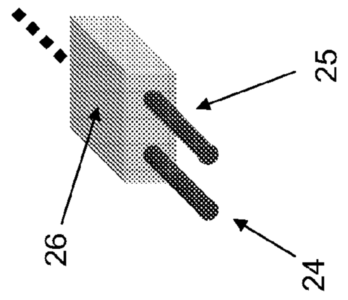

According to FIG. 17, two wire-shaped conductors 24, 25 are positioned in a rod-shaped block of the dielectric 26.

Figure 18:
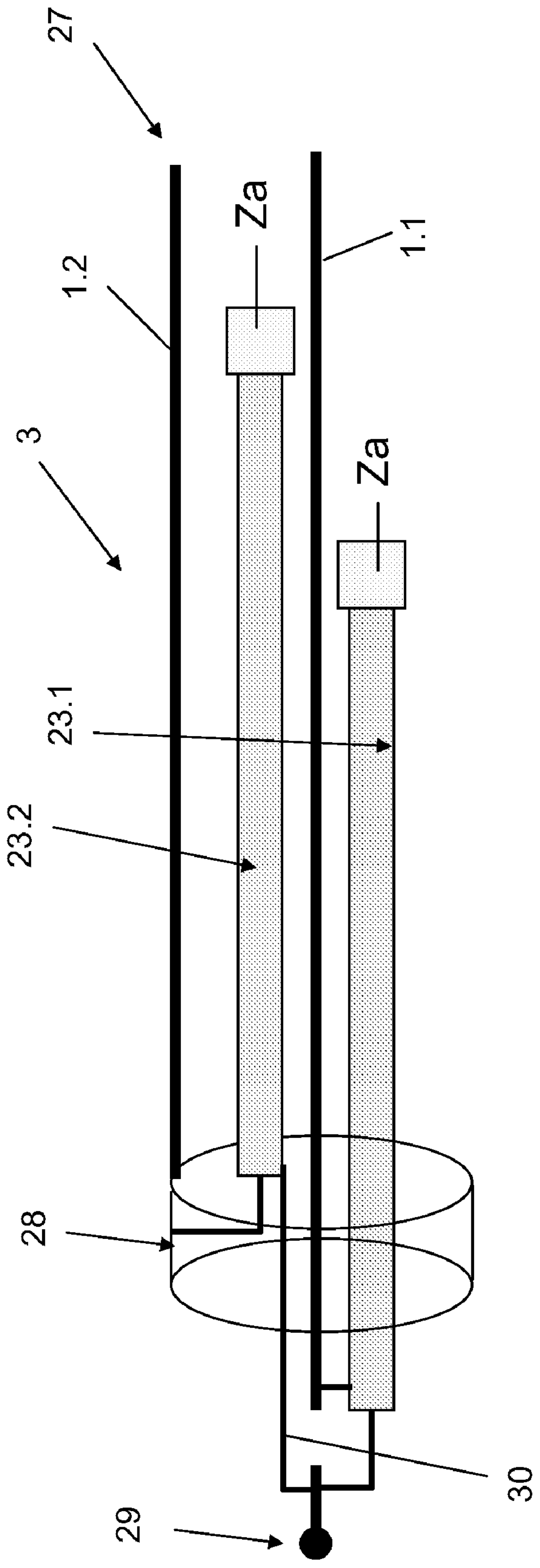
FIG. 18 is a schematic view of an electrode unit having two contact poles and feed lines and waveguides as frequency-dependent transmission systems.

A circuit-related implementation of a frequency-dependent transmission system in an electrode unit having two feed lines 1.1, 1.2 using waveguides 23.1, 23.2, is shown in FIG. 18. The distal end of an electrode unit is shown schematically in the form of a cardiac electrode 27, which has a ring contact pole 28 and a tip pole (tip electrode) 29. The first waveguide 23.1 is connected in the feed line 1.1, and the feed line 1.2 supplies the ring contact pole 28. The second waveguide 23.2 is connected in a line connection 30 between the ring contact pole 28 and tip contact pole 29.

Using the waveguide 23.1, a frequency-dependent line interruption (power cut-off) is achieved at the feed line 1.1. Between the contact poles 28, 28, a frequency-dependent short circuit is caused using the waveguide 23.2. The feed line 1.2 may otherwise also comprise a waveguide, as is the case with the feed line 1.1. In this case, a break point is implemented just before the ring contact pole 28.

Figure 19:
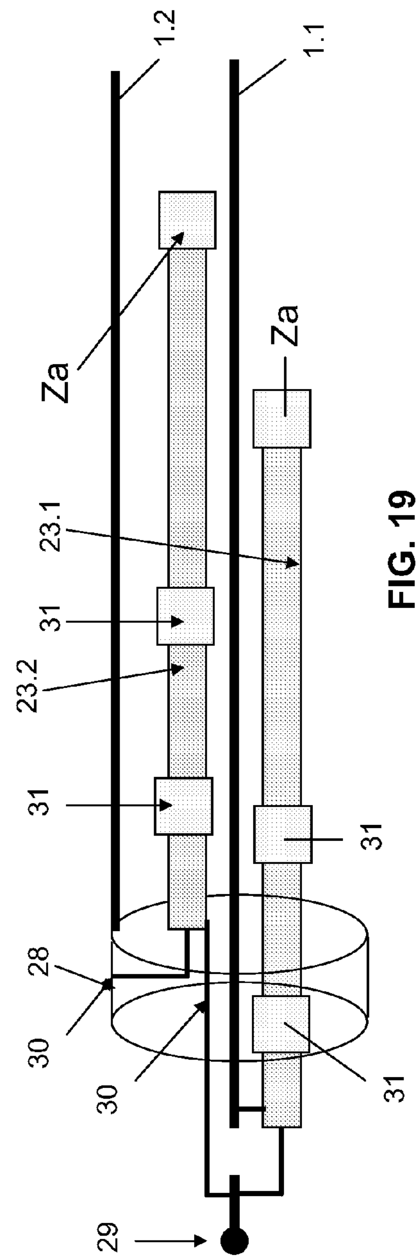
FIG. 19 is an electrode unit analog to FIG. 18, comprising additional networks in the waveguides.

The embodiment of an electrode unit 27 having two feed lines 1.1 and 1.2, a ring contact pole 28, and a tip contact pole 29 shown in FIG. 19 corresponds to the embodiment according to FIG. 18. Similarly, two waveguides 23.1, 23.2 are coupled in the same manner into the feed line 1.1 or line connection 30.

The essential difference is that the frequency-dependent transmission system 3 that is formed can also be used for the operation at several frequencies, because of networks 31 that are integrated in the waveguides 23. Each of the networks 31 interposed in the waveguides 23 is active for a particular MRI frequency, so that a patient having an implanted cardiac electrode designed as that in FIG. 19 has no problems with conventional MRI systems having field strengths of 1.5 T, 3 T, and 7 T.

Figure 21:
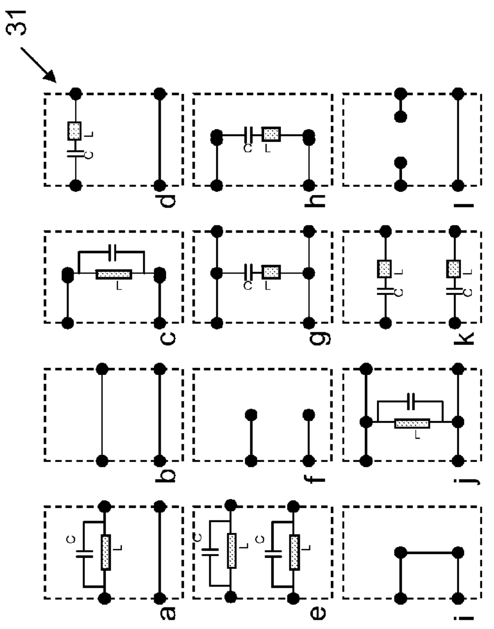
Figure 20:
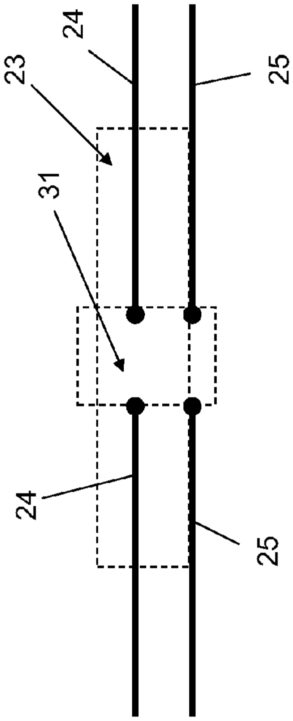
FIG. 20 is a schematic detailed section of a waveguide comprising a network according to FIG. 19, FIG. 21 show wiring diagrams of different variants for the networks according to FIGS. 19 and 20.

FIG. 20, in conjunction with FIG. 21, visualizes the insertion of the networks 31 in the conductors 24, 25 of the waveguides 23. In this way, the conductors 24, 25 are interrupted, and the networks shown in FIGS. 21_a_ to _l_ can be connected to the connecting points 32. As is apparent from the individual illustrations a to l, different short-circuit and break variants (FIGS. 21_b, f, i_, and _l_), and different combinations of interposed parallel LC resonant circuits (FIGS. 21_a, c, e_, and _j_) and of serial LC circuits (FIGS. 21_d, g, h_, and _k_), can be interposed with different effects on the frequency dependence.

Figure 22:
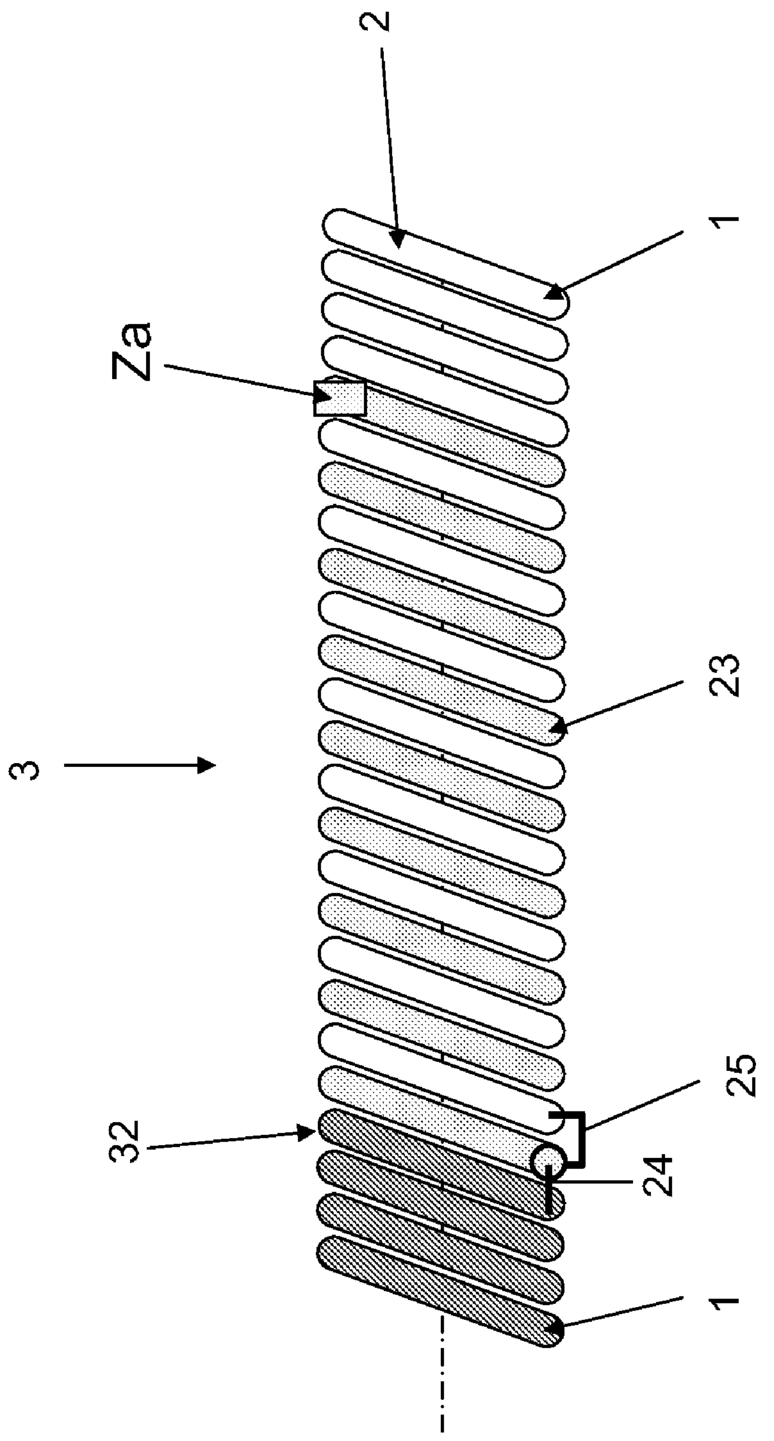
FIG. 22 is a further alternative embodiment of a waveguide integrated in a feed line as a frequency-dependent transmission system.

FIG. 22 shows a waveguide variant of the frequency-dependent transmission system 3, wherein a coiled waveguide 23 having the same diameter and the same helical pitch is used over a certain length of the feed line 1. In this region, the "helical thread" is quasi double-threaded and formed alternately by the helices of the feed line 1 and of the waveguide 23. At the distal end 32 of the waveguide 23, the conductors 24, 25 are connected to the section of the feed line 1 leading toward or away from it. FIG. 22 finally also shows the waveguide terminator Za at the proximal end of the waveguide 23.

Figure 23:
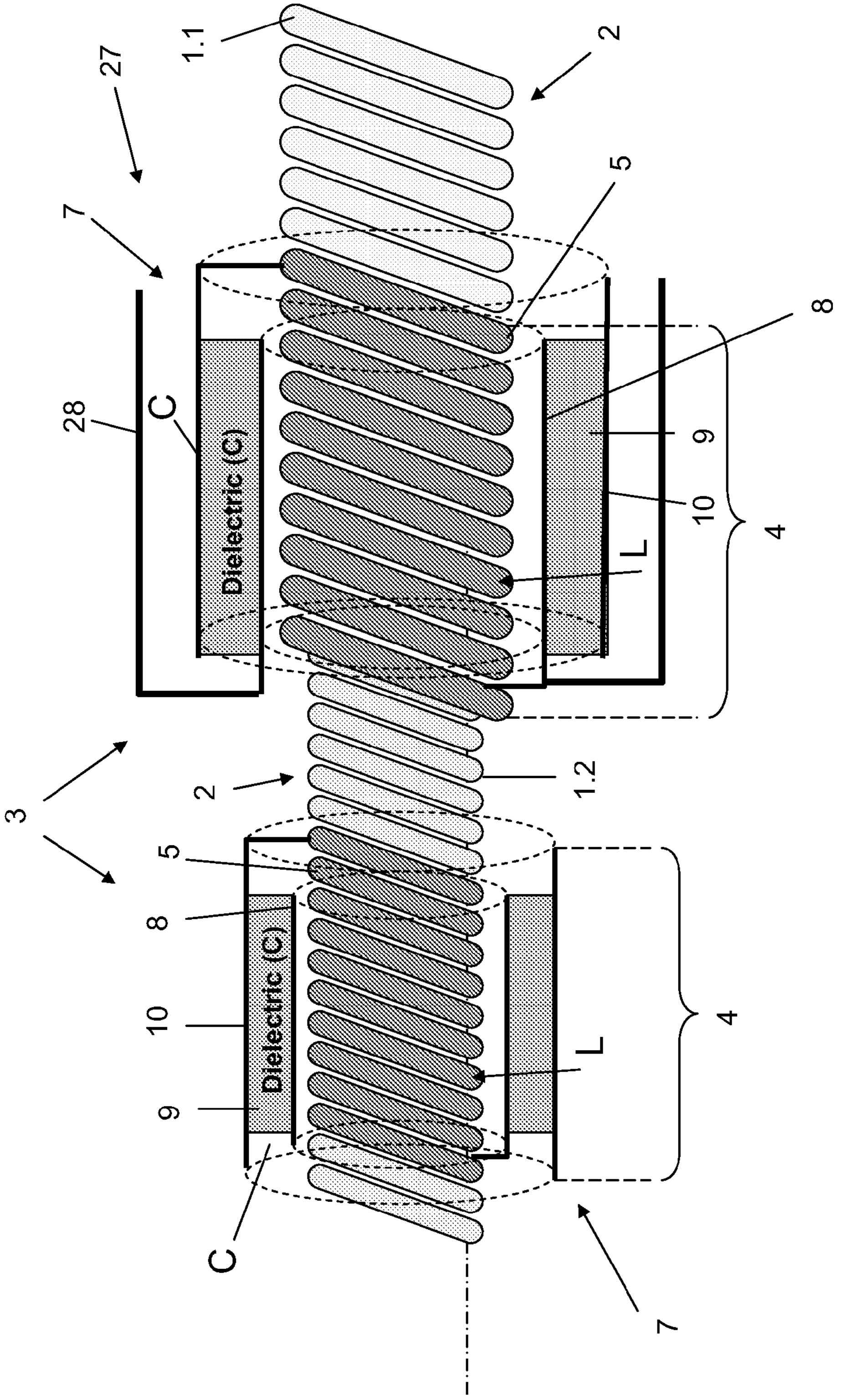
FIG. 23 is a schematic illustration of an electrode unit having inner and outer conductors and frequency-dependent transmission systems associated therewith, FIGS. 24A/B-26A/B are schematic illustrations of electrode units having integrated frequency-dependent transmission systems with the corresponding equivalent circuits.

More complex implementations of electrode units 27 having frequency-dependent transmission systems 3 are shown in FIGS. 23 to 26. FIG. 23, for example, shows a cardiac electrode 27 having a coiled outer conductor as a feed line 1.1 to a ring contact pole 28. In this outer conductor, an inner conductor runs as a feed line 1.2 beyond the distal end of the feed line 1.1 and electrically connects, for example, to a tip electrode (not shown).

At the outer end, the outer feed line 1.1 is designed over a section 4 as an inductor L due to an accordingly highly conductive coating 5. Analogous to FIG. 3, a cylinder capacitor 7 having an inner sleeve 8, dielectric 9, and outer sleeve 10 is positioned around this section 4, the capacitor being located inside the ring contact pole 28. The latter is electrically connected to the inner sleeve 8 of the capacitor 7, which in turn is connected to the distal end of the inductor L. The proximal end is electrically connected to the outer sleeve 10, so that a parallel circuit of the inductance L and capacitance C of the capacitor 7 is located between the feed line 1.1 and ring contact pole 28.

An analogous frequency-dependent transmission system 3 is disposed in the region of the inner feed line 1.2 distally to the transmission system 3 offset in the outer conductor. Again, inductance L is applied in the manner described above within the coiled feed line 1.2, which at the remote terminal coils is electrically connected to the outer or inner sleeve of the cylinder capacitor 7.

Figure 24A:
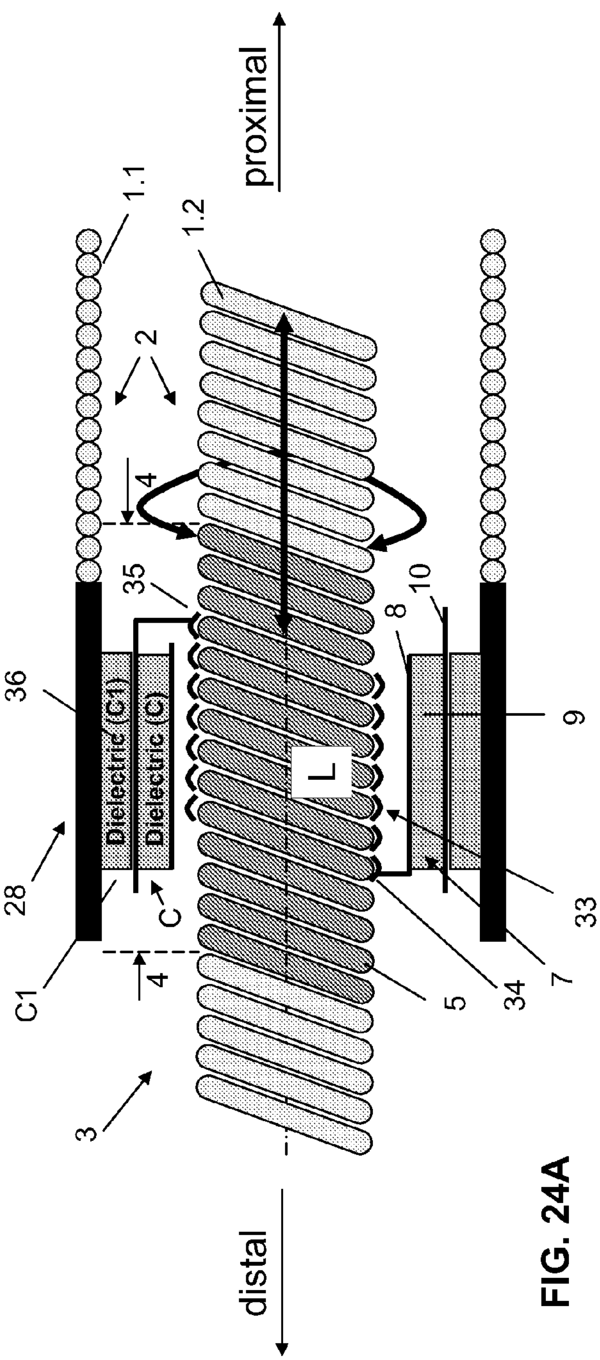
Figure 24B:
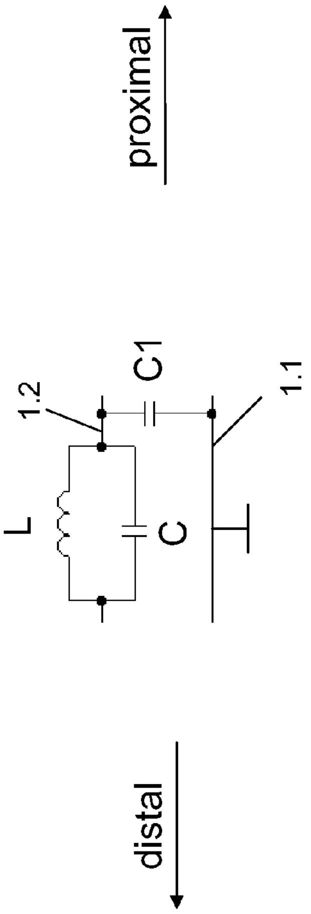

The embodiment shown in FIGS. 24 A and B reflects the implementation of a frequency-dependent transmission system 3 in the form of a frequency-dependent power cut-off along the inner feed line 1.2. of a cardiac electrode having high-pass properties between the outer feed line 1.1 and the inner feed line 1.2. For the coiled inner feed line 1.2, a so-called pitch provider 33 is integrated in the transmission system 3. This pitch provider 33 is designed in the form of an internal thread, in which the section 4 of the inner feed line 1.2 designed as an inductor L in the manner described can be rotated and is mounted displaceably in the axial direction during rotation. The last convolutions 34, 35 of the pitch provider 33 in the distal and proximal directions, respectively, are designed to be electrically conductive and contact the helix forming the inductor L with the windings guided therein. The distal convolution 34 is electrically connected to the inner sleeve 8 of a cylinder capacitor 7 disposed around the inductor L, and the proximal convolution 35 has the corresponding outer sleeve 10. The capacitor C formed by the dielectric 9 between the two sleeves 8, 10 is therefore connected in parallel to the inductor L between the two convolutions 34, 35 in the feed line 1.2 to the tip contact pole 29, as is shown in the equivalent circuit according to FIG. 24B. The ring contact pole 28, which is connected by way of a further dielectric 36 to the outer sleeve 10 of the capacitor 7, forms a capacitive coupling C1 between the outer feed line 1.1 or the ring contact pole 28 and the inner feed line 1.2.

Figure 25A:
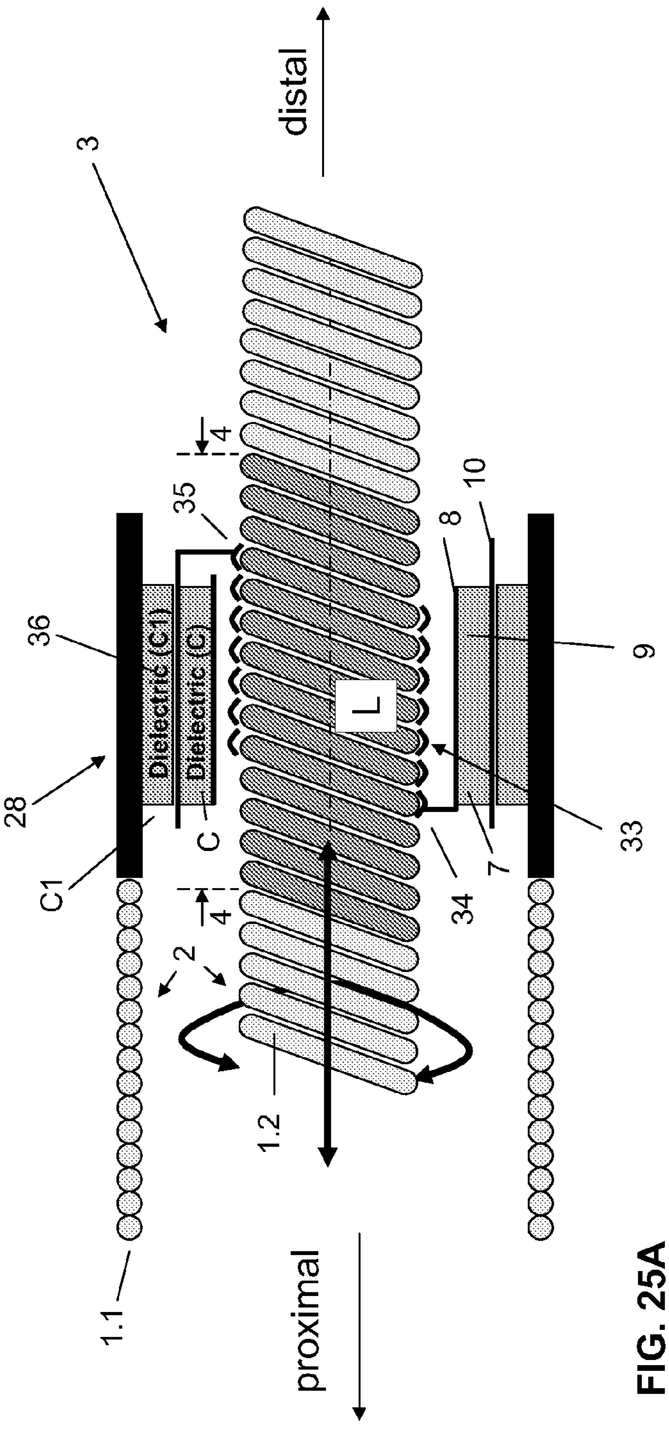
Figure 25B:
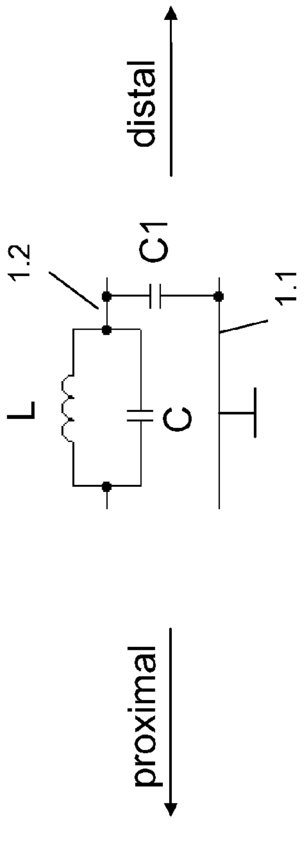

The embodiment shown in FIG. 25 differs from that of FIG. 24 only in that the energy consumed by the electrode lead has contact with different electronic components. In the present case, the energy arrives from the proximal end and, in FIG. 25, first comes in contact with a voltage divider, while in FIG. 24 the energy first comes in contact with the bypass capacitor and the remaining energy is attenuated by the serial resonant circuit (rejection circuit).

Figure 26A:
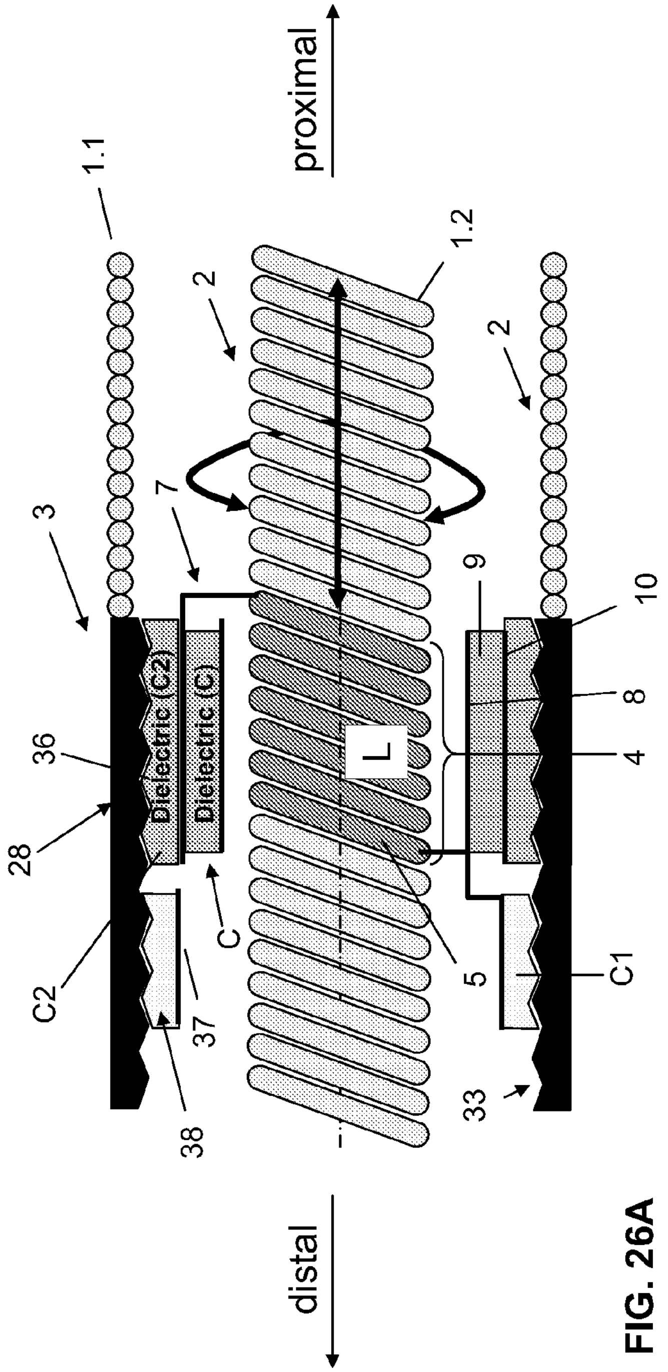
Figure 26B:
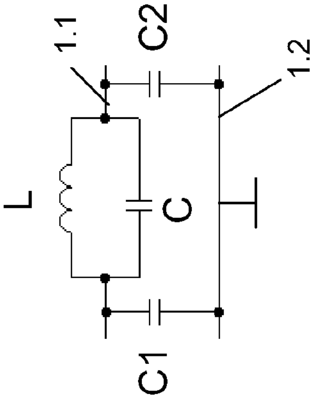

FIG. 26 shows sections of an electrode unit, wherein a low-pass filter for the inner feed line 1.2 is implemented for the coiled inner feed line 1.2 having an integrated pitch provider 33. In detail, inductance L is again applied over a section 4 by a highly conductive coating or the like to the coiled feed line 1.2. The last convolutions of the inductor L in the proximal and distal directions, respectively, are electrically connected to the inner sleeve 8 or outer sleeve 9 of a cylinder capacitor 7, which is composed analogous to FIG. 3, so that again a parallel circuit of L and C is obtained (see FIG. 26B).

A ring contact pole 28, which is connected to the implant by the outer coiled feed line 1.1, is disposed around this assembly. On the inside of the ring contact pole 28, a pitch provider 33 is configured in the form of convolutions, which is capacitively coupled to the outer sleeve 10 of the cylinder capacitor 7 by way of a dielectric 36. In this way, the capacitance C2 is implemented between the feed lines 1.1 and 1.2, as is apparent in FIG. 26*b*.

Furthermore, a ring sleeve 37 that is electrically connected to the inner sleeve of the cylinder capacitor 7 is disposed distally in front of the cylinder capacitor 7 inside the ring contact pole 28, which in turn is capacitively coupled to the ring contact pole 28 with the capacitance C1 by way of a dielectric 38. In this way, the two feed lines 1.1, 1.2 are also coupled capacitively by way of the capacitor C1 distally of the LC resonant circuit (see FIG. 26*b*).

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE NUMERALS

1 Feed line, starting with FIG. 7: 1.1, 1.2 31 Network
2 Helix 32 Distal end
3 System 33 Pitch provider
4 Section 34 Convolution—distal
5 Coating 35 Convolution—proximal
6 Resonant circuit 36 Dielectric
7 Capacitor 37 Ring sleeve
8 Inner sleeve 38 Dielectric
9 Dielectric
10 Outer sleeve l Length of waveguide
11 Trim element L Inductance, inductor
12 Sensor C Capacitance, capacitor
13 f/V converter Z1 Impedance
14 Demodulator Z2 Impedance
15 Cutoff value transducer G Ground
16 Low-pass filter Za Terminating impedance
17 Fixing helix
18 Housing projection
19 Inside lumen
20 Shoulder
21 Electrical connection
22 Widened windings
23 Waveguide
24 Conductor
25 Conductor
26 Dielectric
27 Cardiac electrode
28 Ring contact pole
29 Tip contact pole
30 Line connection

What is claimed is:

1. An electrode unit for carrying current or voltage between an implantable electromedical device and a treatment and/or diagnosis site in the human body, comprising:

at least one current-/voltage-carrying feed line;

at least one electrical contact pole coupled to a body part wherein said at least one electrical contact pole is coupled with said at least one current-/voltage-carrying feed line;

wherein the at least one current-/voltage-carrying feed line is associated with at least one frequency-dependent transmission system, wherein said at least one frequency-dependent transmission system at least partially filters out therapeutically and/or diagnostically undesirable signals in at least one defined frequency range;

wherein the at least one frequency-dependent transmission system is formed directly by one or more sections of the at least one current-/voltage-carrying feed line;

wherein the frequency-dependent transmission system is formed by a higher-conductive section of a helix of the at least one current-/voltage-carrying feed line.

2. The electrode unit according to claim 1, wherein the higher-conductive section has at least twice the conductivity as compared to a remaining portion of the at least one current-/voltage-carrying line, and wherein the higher-conductive section comprises a highly conductive coating or doping of the higher-conductive section of the helix.

3. The electrode unit according to claim 1, wherein the higher-conductive section of the helix comprises windings insulated on an outside of said windings.

4. An electrode unit according to claim 1, wherein the higher-conductive section of the helix forms an inductance-capacitance resonant circuit with a parallel connected capacitor as the frequency-dependent transmission system.

5. The electrode unit according to claim 4, wherein the capacitor of the inductance-capacitance resonant circuit is formed by a cylinder capacitor disposed around the higher-conductive section of the helix and/or inside the higher-conductive section of the helix.

6. An electrode unit for carrying current or voltage between an implantable electromedical device and a treatment and/or diagnosis site in the human body, comprising:

at least one current-/voltage-carrying feed line;

at least one electrical contact pole coupled to a body part wherein said at least one electrical contact pole is coupled with said at least one current-/voltage-carrying feed line;

wherein the at least one current-/voltage-carrying feed line is associated with at least one frequency-dependent transmission system, wherein said at least one frequency-dependent transmission system at least partially filters out therapeutically and/or diagnostically undesirable signals in at least one defined frequency range; and, wherein the control voltage can be generated by programming the implantable electromedical device, or by a sensor configured to detect therapeutically and/or diagnostically undesirable signals.

7. The electrode unit according to claim 6, wherein the sensor is disposed in the implanted electromedical device or associated with the at least one current-/voltage-carrying feed line.

8. The electrode unit according to claim 7, wherein the sensor is a field sensor for electrical, magnetic and/or electromagnetic fields, in particular a dipole, wherein the electromagnetic fields are static and/or alternating fields.

* * * * *